(12) United States Patent
Chambers

(10) Patent No.: US 9,700,446 B2
(45) Date of Patent: Jul. 11, 2017

(54) STENT POSITIONING SYSTEM AND METHOD

(75) Inventor: Jeffrey W. Chambers, Maple Grove, MN (US)

(73) Assignee: Chambers Technology Inc., Maple Grove, MN (US)

( * ) Notice: Subject to any disclaimer, the term of this patent is extended or adjusted under 35 U.S.C. 154(b) by 656 days.

(21) Appl. No.: 13/597,111

(22) Filed: Aug. 28, 2012

(65) Prior Publication Data

US 2013/0006344 A1 Jan. 3, 2013

Related U.S. Application Data

(60) Division of application No. 10/812,250, filed on Mar. 29, 2004, now Pat. No. 8,252,034, which is a continuation-in-part of application No. 09/754,223, filed on Jan. 5, 2001, now abandoned.

(51) Int. Cl.
*A61F 2/958* (2013.01)
*A61F 2/82* (2013.01)

(52) U.S. Cl.
CPC ........ *A61F 2/958* (2013.01); *A61F 2002/821* (2013.01)

(58) Field of Classification Search
CPC .. A61F 2002/821; A61F 2/958; A61F 2/2427; A61F 2/954; A61F 2/848; A61F 2250/0098; A61F 2002/9511; A61F 2/95
USPC ................. 623/1.11, 1.12; 604/104; 600/585
See application file for complete search history.

(56) References Cited

U.S. PATENT DOCUMENTS

| | | | |
|---|---|---|---|
| 5,349,964 A * | 9/1994 | Imran et al. | 600/585 |
| 5,607,444 A | 3/1997 | Lam | |
| 5,683,451 A | 11/1997 | Lenker et al. | |
| 5,749,890 A | 5/1998 | Shaknovich | |
| 5,824,041 A * | 10/1998 | Lenker et al. | 606/195 |
| 6,027,520 A * | 2/2000 | Tsugita | A61F 2/01 606/200 |
| 6,093,199 A | 7/2000 | Brown et al. | |
| 6,168,621 B1 | 1/2001 | Vrba | |
| 6,280,413 B1 * | 8/2001 | Clark et al. | 604/104 |
| 6,409,755 B1 | 6/2002 | Vrba | |
| 6,458,151 B1 | 10/2002 | Saltiel | |
| 6,532,380 B1 | 3/2003 | Close et al. | |
| 6,652,555 B1 | 11/2003 | VanTassel et al. | |
| 2002/0068866 A1 | 6/2002 | Zikorus et al. | |
| 2004/0073291 A1* | 4/2004 | Brown | A61F 2/915 623/1.34 |
| 2005/0154447 A1* | 7/2005 | Goshgarian | 623/1.15 |

* cited by examiner

*Primary Examiner* — Brian Pellegrino
(74) *Attorney, Agent, or Firm* — Dicke, Billig & Czaja, PLLC

(57) ABSTRACT

A stent combined with a positioning apparatus to effectively place the stent at a precise deployment site within a narrowed vascular region such as an artery. The stent is maneuvered through the vessel and is guided by a guiding catheter up the vessel to where the narrowing is located. Upon exiting the guiding catheter and approaching the deployment site within the coronary artery, a deployment site locator expands to contact the vascular structure and, thereby, effectively position the stent at the deployment site within the narrowed vessel. This system apparatus and method is particularly useful for stent placement at an ostium (origin) of a vessel.

19 Claims, 9 Drawing Sheets

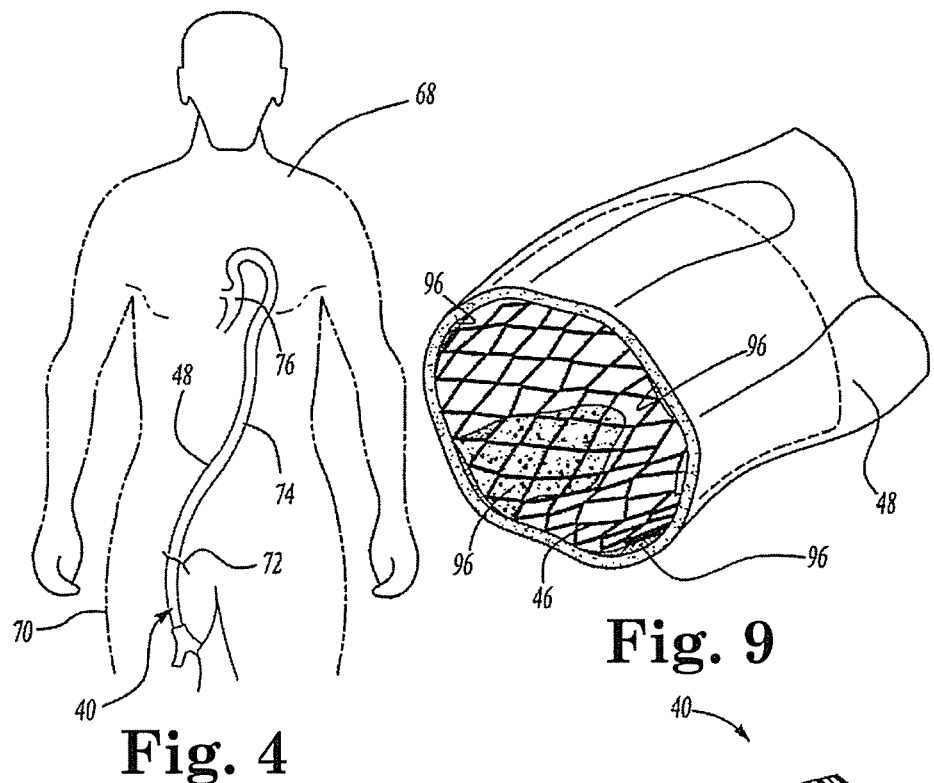
Fig. 4
Fig. 9
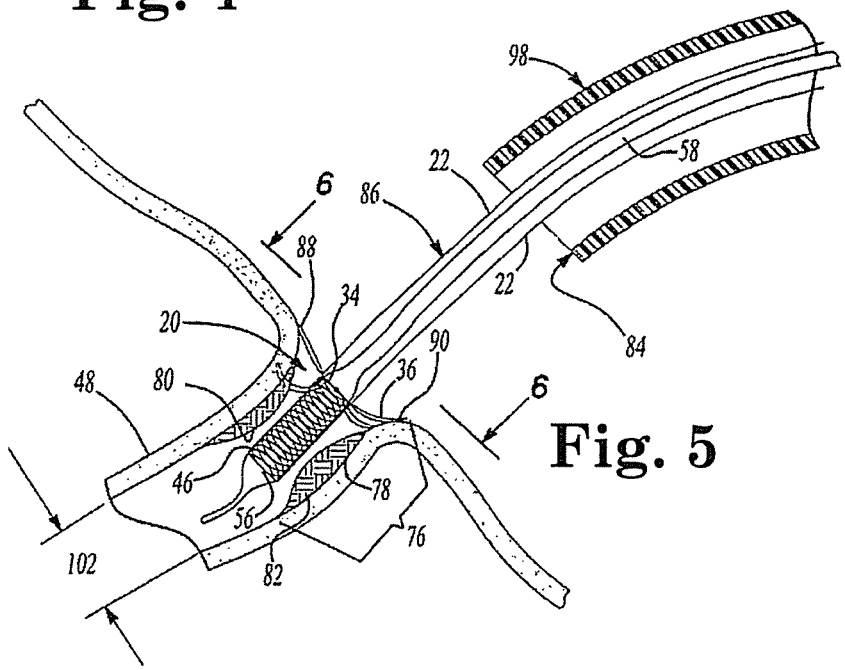
Fig. 5

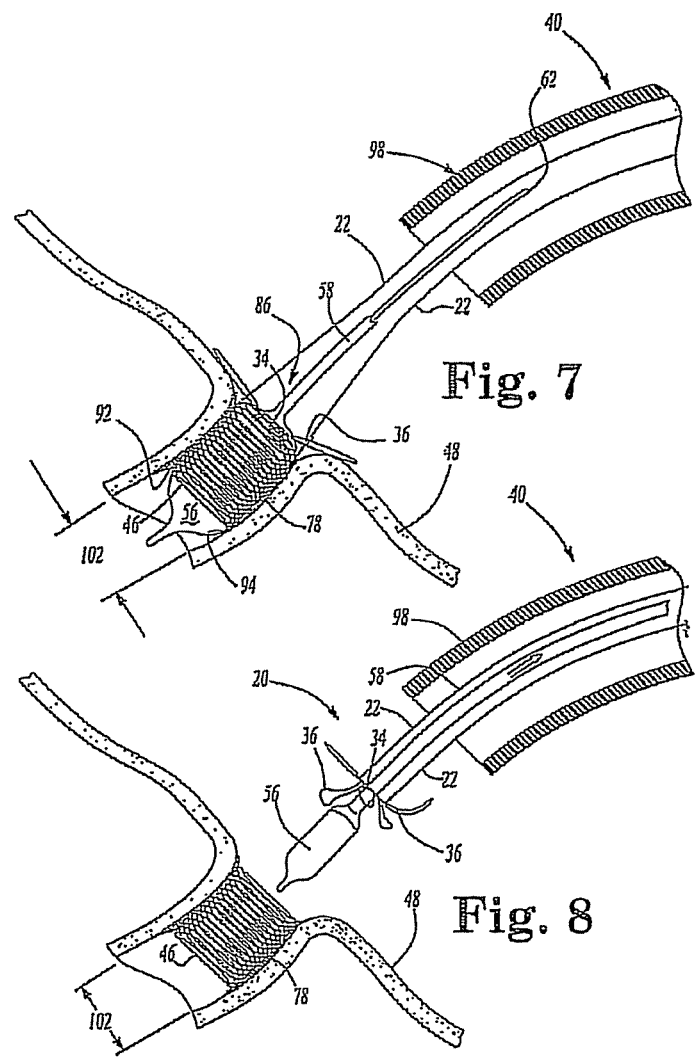

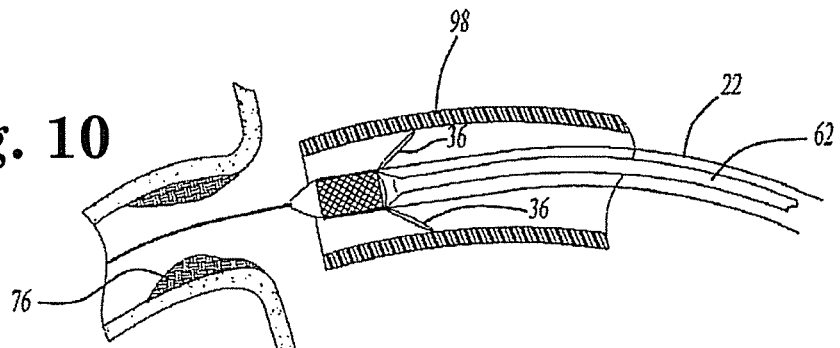
Fig. 10
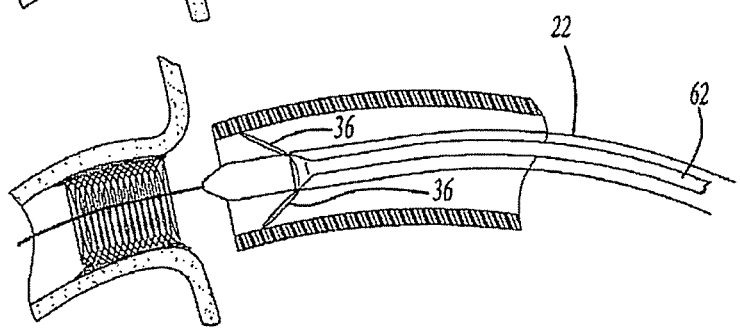
Fig. 11
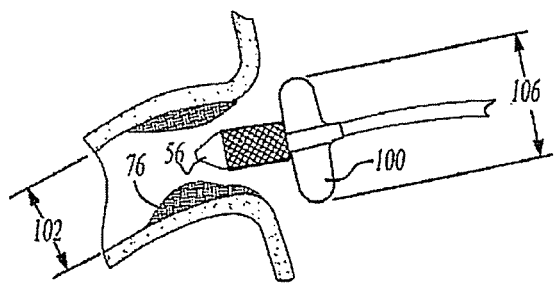
Fig. 12
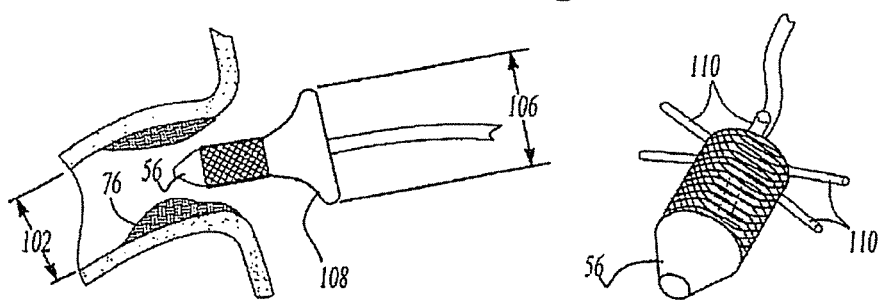
Fig. 13
Fig. 14

STENT POSITIONING SYSTEM AND METHOD

CROSS-REFERENCE TO RELATED APPLICATIONS

This application is a continuation-in-part of U.S. patent application Ser. No. 09/754,223, entitled "Apparatus And Method To Position A Stent" filed on Jan. 5, 2001 and is also a divisional of U.S. patent application Ser. No. 10/812,250, entitled "A Method Of Positioning A Stent Using Rods" filed on Mar. 29, 2004, now U.S. Pat. No. 8,252,034.

FIELD OF THE INVENTION

The present invention relates generally to an intravascular stent and, in particular, to quick, effective, and accurate positioning of a stent within a stenosed (narrowed) vascular region.

BACKGROUND OF THE INVENTION

A stent is an intravascular prosthesis implanted in a blood vessel to maintain vascular patency in an artery, vein, lymph, or another duct in the body such as the biliary duct, ureter, or urethera (collectively referred to as vessels). For example, a stent is often a necessary treatment for atherosclerosis. Atherosclerosis is an accumulation of lipids, also known as lesions, plaques, or atheromas, in the intimal or inner layer of an affected artery. The resulting intimal thickening of lipids restricts arterial blood flow, disrupting the function of or permanently damaging the nourished organ such as the heart. Typically, the accumulation of lipids is localized and occurs in coronary, renal, cerebral, or peripheral arteries.

Treatments for atherosclerosis focus on improving blood flow through narrowed arteries. One method, balloon angioplasty, simply expands a balloon catheter to compress lipid plaque against the artery wall. Unfortunately, scar tissue (neointimal proliferation) often builds up over time and renarrows the artery. This is called restenosis. To reduce the chance of restenosis, stents are often implanted. A stent is an expandable meshed metal tube used to support a narrowed artery after angioplasty. In this procedure, the stent is deployed at the center of the lipid accumulation. Once a deployment site is identified, the stent is maneuvered through the vessel to that site. Physicians typically use fluoroscopic x-ray and injection of radiopaque contrast and marking bands on the stent balloon to determine if the stent is positioned at the narrowed region. Once positioned, the stent expands to compress the lipids, thereby opening the artery and increasing blood flow. Stenting, as described in the prior art, significantly reduces restenosis of the artery compared to balloon angioplasty alone.

Ineffective and inaccurate stent placement can result in a poor overall patient outcome. For instance, if the stent is deployed too distal to the vessel narrowing, ineffective plaque compression can result. Further, a higher rate of restenosis can also be expected. If the stent is placed too proximal to a narrowing at the aorta origin (ostium), the stent cam hang into the aorta and a thrombus (clot) can form on the stent. Placement of the stent too proximal can also result in inappropriate and unintended blockage of another blood vessel.

Thus, an apparatus and method is needed to more effectively and accurately position a stent at a desired deployment site within the narrowed area of a vessel, thereby improving overall patient outcome.

SUMMARY

One aspect of the present invention relates to an intravascular stent deployment site locator comprising a base, a plurality of rods affixed to the base, each one of the plurality of rods having a distal end. In the embodiment, the plurality of rods extend outward radially relative to one another to contact vascular structures proximate an ostium in order to locate the ostium. Additionally, the deployment site locator is capable of transitioning between an expanded state and a collapsed state, wherein the collapsed state includes the plurality of rods extending outward radially from one another to a lesser extent than in the expanded state.

Another aspect of the present invention relates to a stent placement system for use with a guiding catheter forming a lumen. The system includes a deployment site locator and a stent delivery device. In particular, the deployment site locator includes a base, and a plurality of rods affixed to the base, wherein each one of the plurality of rods has a distal end. The deployment locator is adapted to provide an expanded state in which the plurality of rods extend outward radially from the base to contact vascular structures proximate an ostium in order to locate the ostium. The stent placement system is such that the stent delivery device and deployment site locator are both configured to deliver a stent to a deployment location relative to the deployment site locator.

In one embodiment, the deployment site locator or regulator can be fixed relative to the stent, for example by frictionally engaging the stent delivery device at an appropriate structure such as a distal end of the stent, a stent balloon, or a stent catheter. Another embodiment of the stent placement system includes the deployment site locator being adjustably located relative to the stent.

The present invention also relates to a method of deploying an intravascular stent. The method includes delivering a distal end of a guiding catheter adjacent an ostium of a vessel to be stented. Further, the method comprises guiding a deployment site locator through the guiding catheter, the deployment site locator including a base and a plurality of rods affixed to the base. The plurality of rods are extended from the distal end of the guiding catheter and a position of the ostium is determined by contacting structures proximate the ostium with a least one of the plurality of rods. The method also comprises delivering a stent through the guiding catheter to a desired stent location, wherein the desired stent location is based upon the determined position of the ostium. Once the stent is properly located, the stent is deployed at the desired stent location

BRIEF DESCRIPTION OF THE DRAWINGS

The foregoing objects, advantages, and features of the present invention, as well as other objects and advantages, will become apparent with reference to the description and drawings below, in which like numerals represent like elements and in which:

FIG. 4 is a front view of a patient illustrating insertion of a stent into a human body and a direction the stent follows to a narrowed vascular region or deployment site.

FIG. 5 is a side cross-sectional view of a vessel with the positional apparatus of FIG. 1 and a stent at a deployment site.

FIG. 7 is a side cross-sectional view relating to FIG. 5 showing an expanded balloon catheter and a stent being deployed within a vessel.

FIG. 8 is a side cross-sectional view relating to FIG. 7 of the deployed stent and the removal of the stent placement device and catheter.

FIG. 9 is a side perspective view of a stent as deployed within a narrowed vessel.

FIG. 10 shows a side perspective view of the stent, the catheter balloon, and the positional device of FIG. 1 while moving toward the narrowed vascular region.

FIG. 11 shows a side perspective view of the catheter balloon and positional device of FIG. 1 while moving away from the stented vascular region.

FIG. 12 shows an alternative embodiment of the present invention using a new type of balloon catheter with an annular ring.

FIG. 13 shows an alternative embodiment of the present invention using a flange as the deployment site regulator.

FIG. 14 shows an alternative embodiment of the present invention using rods as the deployment site regulator.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way intended to be limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The present invention generally relates to improved stent placement. Although the preferred embodiment describes use within an artery, the invention could be applied to any region of a person or an animal where a stent is to be deployed in a vessel. As used throughout this description, proximal and distal orientation relationships are in relation to a surgeon utilizing the invention as described herein.

Figure 1:
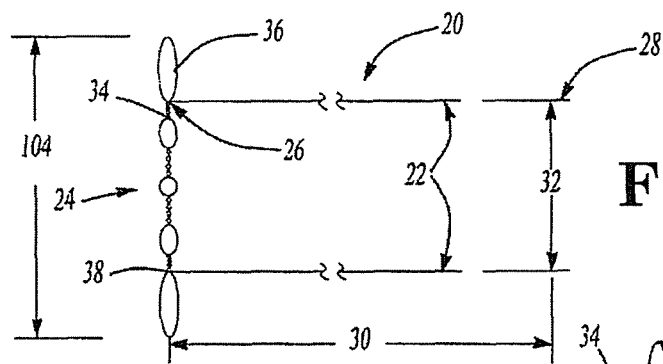
FIG. 1 is a side elevational view of a positional apparatus for a stent in accordance with the present invention.

FIG. 1 illustrates a stent positioning apparatus 20 in one of its preferred embodiments and is not intended to limit the apparatus in any way. The preferred stent positioning apparatus 20 consists of a plurality of stabilizing wires 22 and a deployment site regulator 24. The stabilizing wires 22 have a distal end 26 and a proximal end 28. Distal end 26 and proximal end 28 are separated by a stabilizing wire length 30 with a stabilizing wire spacing diameter 32. The stabilizing wire length 30 is of sufficient length to reach a narrowed region within either a primary blood vessel or a coronary artery. Preferably, the stabilizing wire length 30 is approximately 120-170 centimeters long and the stabilizing wire spacing diameter 32 is approximately 0.3 centimeters wide, although other dimension are equally acceptable.

The deployment site regulator 24 is attached to the distal end 26 of the stabilizing wires 22. Attachment can be by means of frictional engagement, elastic bands, springs, adhesives, welds, clasps, screws, snaps, magnets, polymer bondings, or contiguous with any stent placement element such as a stent 46, a balloon catheter 54 or the stabilizing wires 22. In one embodiment, the deployment site regulator 24 comprises a spring 34 and a plurality of wire loops 36. The spring 34 is attached to the stabilizing wires 22 such that the spring 34 and stabilizing wires 22 will not become detached during a stent procedure. The wire loops 36 extend outwardly from, and parallel to, spring 34. The wire loops 36 are attached to spring 34 at an attachment point 38. Preferably, wire loops 36 are permitted unrestricted rotation about attachment point 38 in relation to spring 34. The unrestricted rotation allows wire loops 36 to be maneuvered through a guiding catheter 40, having a guiding catheter sheath 98 (FIG. 5), to or from the narrowed region of the vessel during the stent procedure. Wire loops 36 have a surface such that contact with the interior walls of guiding catheter 40 does not impede the progress of wire loops 36 through guiding catheter 40, but is sufficient to frictionally engage a vessel 48 interior wall (FIG. 4) without damaging the vessel 48.

In FIG. 5, vessel 48 has a vessel diameter 102 that is sufficiently smaller than a wire loop diameter 104 (FIG. 6) in its natural position. Preferably, wire loops 36 are made of a nitinol wire frame. Alternatively, the wire loops 36 may be made of another type of wire frame or material, provided the wire loops 36 made with the alternative material are able to perform the same functions as the wire loops 36 with the nitinol wire. A further embodiment, described below and shown in FIG. 12, removes the wire loops 36 and instead uses a balloon catheter with an expanded diameter annular ring to engage adjacent structures of the vessel 48.

Other embodiments of the deployment site regulator 24 could include any device that can make its way through the guiding catheter sheath 98 in a retracted position, but can expand to engage adjacent structures of the vessel 48. These could include a rubber flange 108 (FIG. 13) or outward radiating rods 110 (FIG. 14), similar to those described subsequently in other embodiments, instead of loops.

Figure 2:
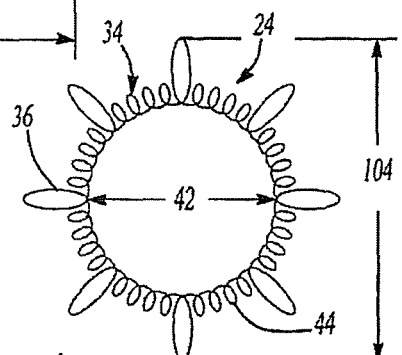
FIG. 2 is a front cross-sectional view of the positional apparatus of FIG. 1.

FIG. 2 illustrates the deployment site regulator 24 with more specificity. Preferably, the stabilizing wires 22 and spring 34 are circular in shape and the spring 34 has a diameter 42 approximately equal to the stabilizing wire spacing diameter 32. Spring 34 is a closed loop that consists of a plurality of coils 44. The coils 44 are situated adjacent to one another in equal spacing around the entire periphery of spring 34. Coils 44 permit spring 34 to be expanded during the stent procedure. Wire loops 36 are attached to spring 34 between coils 44. Preferably, wire loops 36 are equally spaced around the entire periphery of spring 34. FIG. 2 is a non-limiting example which depicts eight wire loops 36 around the entire periphery of spring 34. Alternatively, the deployment site regulator 24 may contain more or fewer wire loops 36 as long as the proper frictional engagement is provided by wire loops 36 to accurately position the stent 46 (FIG. 3) at the deployment site within the vessel 48. In one preferred embodiment, the deployment site regulator 24 is releasably attached to the stent 46 using a frictional engagement. As the stent 46 expands to the deployed position, the deployment site regulator 24 is released from the stent 46. Elastic bands, springs, adhesives, welds, clasps, screws, snaps, magnets, polymer bondings, or contiguous with the stent 46 or the stabilizing wires 22 can be used rather than frictional engagement to releasably attach the stent 46 to the deployment site regulator 24. A specially shaped catheter is described below in an alternative embodiment.

Figure 3:
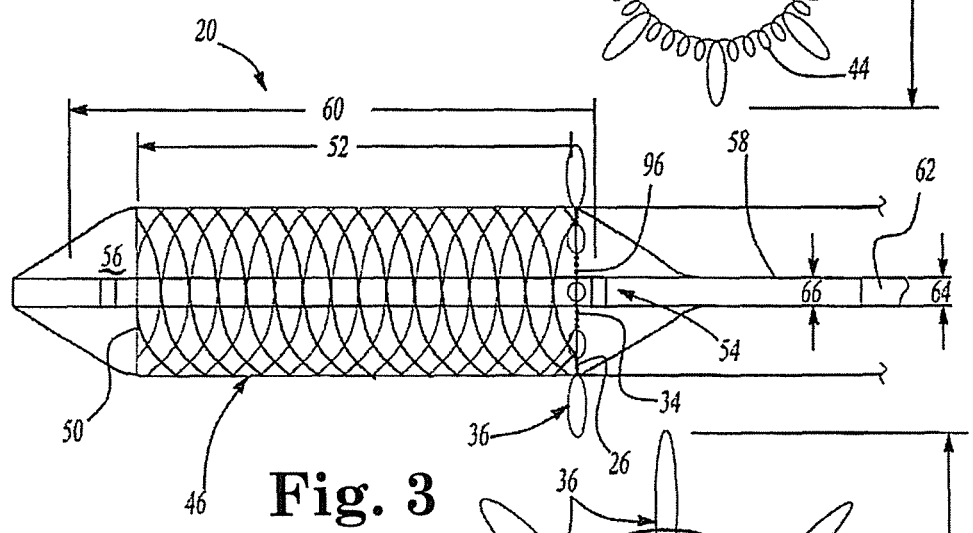
FIG. 3 is a side elevational view of a stabilizing wire attached to the positional apparatus as shown in FIG. 1 and a stent coaxially mounted with a balloon catheter.

The interconnection of stent 46 to stabilizing wires 22 is more clearly illustrated in FIG. 3. Stent 46 is generally a hollow, cylindrical prosthesis that comprises thin walled, tubular members that define a narrow web-like mesh. Stent 46 has a stent distal end 50 and a stent proximal end 96. Stent proximal end 96 of stent 46 is attached to spring 34 at distal end 26 of the stabilizing wires 22. Stent 46 has a stent length 52 of approximately eight to thirty-eight millimeters. Extending throughout the hollow center of stent 46 and stabilizing wires 22 is a stent delivery device, in this case, a balloon catheter 54. Balloon catheter 54 comprises a balloon 56 and a balloon shaft 58. Balloon 56 is releasably mounted and centered within stent 46 and has a balloon length 60. The balloon length 60 will correspond to the stent length 52 and has an overhang of approximately 0.1-0.2 millimeters beyond the stent 46. Alternatively, the balloon length 60 may be equal to or smaller than the stent length 52 as long as balloon 56 is capable of inflating to effectively expand stent 46. Within balloon 56 is a balloon guidewire 62. Balloon guidewire 62 has a balloon guidewire diameter 64. In the preferred embodiment, balloon guidewire diameter 64 is 0.14 centimeters and is 300 cm long.

Balloon shaft 58 has a balloon shaft diameter 66. In the preferred embodiment, balloon shaft diameter 66 is approximately 0.8 millimeters.

In FIG. 4, a non-limiting example of the inventive apparatus is depicted in which guiding catheter 40 is inserted into a human body 68. Typically, guiding catheter 40 is inserted or cannulated into the vessel 48 which is located in a leg 70 of the human body 68. A portion of guiding catheter 40 remains outside of the human body 68 while the remainder of guiding catheter 40 is inserted into human body 68. Guiding catheter 40 enters human body 68 at an incision point 72 and follows through vessel 48 along a path 74. Vessel 48, at incision point 72, is a femoral artery that becomes an iliac artery and then the aorta artery at the point where the iliac arteries merge. Guiding catheter 40 follows path 74 until it reaches a point near the primary coronary arteries of a heart where a narrowed vascular region 76 is located.

In FIG. 5, the proximal portion of vessel 48 is enlarged to depict its origin, or ostium, and the positioning of stent 46 within the narrowed vascular region 76, the site of deployment. Narrowed vascular region 76 consists of an accumulation of lipids 78 that form large patches (atherosclerotic plaques) 80 and 82 on the interior walls of vessel 48. In many instances, patch 80 almost contacts patch 82. Narrowed vascular region 76 represents the location of the highest concentration of lipids 78 in which patches 80 and 82 restrict the greatest amount of blood flow through vessel 48.

To perform the stent procedure, guiding catheter 40, as explained earlier, is first inserted into human body 68 and manipulated through vessel 48 to a holding position 84 near the entry of vessel 48 and the narrowed vascular region 76. Next, stent 46 and balloon 56 are connected to the stent positioning apparatus 20 outside the human body 68. A stent-balloon catheter combination 86 with the stent positioning apparatus 20 attached is inserted into and manipulated through the guiding catheter sheath 98. During the manipulation through guiding catheter sheath 98, wire loops 36 contact the interior wall and are forced into a rearward trailing position with respect to stent 46, as illustrated in FIG. 10. Stent-balloon catheter combination 86 exits guiding catheter 40 at holding position 84. Upon exiting guiding catheter 40, wire loops 36 return to an approximately perpendicular position with respect to stent 46. The stent-balloon catheter combination 86 is then manipulated toward narrowed vascular region 76. Upon nearing narrowed vascular region 76, the target deployment site, the wire loops 36 begin to frictionally engage the adjacent walls of vessel 48 at engagement points 88 and 90. The frictional engagement of the wire loops 36 with the walls of vessel 48 adjacent to the deployment site suspends the forward movement of stent-balloon catheter combination 86 through vessel 48. The forward movement of stent-balloon catheter combination 86 is suspended at the deployment site and stent-balloon catheter combination 86 is centered directly within narrowed vascular region 76 as illustrated more clearly in the cross-sectional view of FIG. 6.

Figure 6:
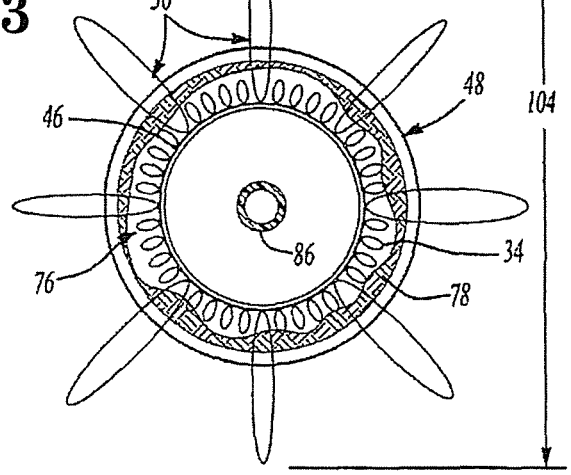
FIG. 6 is a front cross-sectional view, taken along line 6-6 of FIG. 5.

FIG. 6 illustrates the accumulation of lipids 78 around the entire interior periphery of vessel 48 with stent-balloon catheter combination 86 located in the center of vessel 48 at the deployment site. Once stent-balloon catheter combination 86 is positioned within the deployment site of narrowed vascular region 76, balloon 56 is inflated, as illustrated in FIG. 7. When balloon 56 begins to inflate, the exterior of balloon 56 contacts the interior of stent 46 and outwardly forces stent 46 into an expanded position. As stent 46 expands with the inflation of balloon 56, spring 34 correspondingly expands with stent 46 to expansion points 92 and 94 in FIG. 7. As balloon 56 inflates, it applies pressure on lipids 78. Since lipids 78 are a waxy type material, lipids 78 succumb to the pressure of balloon 56 and, thereby, compress against the walls of vessel 48. The compression of lipids 78 reduces the blockage and expands the diameter of vessel 48 to restore vessel patency or blood flow through vessel 48.

In FIG. 8, with the stent 46 in place, balloon 56 is deflated and balloon catheter 54 with the stent positioning apparatus 20 is retracted through the guiding catheter 40 for removal from human body 68. Guiding catheter 40 is then removed from human body 68. FIG. 11 illustrates the removal of the balloon catheter 54 and the stent positioning apparatus 20. As before, wire loops 36 contact the interior wall of vessel 48 and are forced into a rearward trailing position with respect to the direction of removal. Stent 46 remains within vessel 48, as illustrated in FIG. 9, as a prosthesis to repair or strengthen vessel 48 and prevent restenosis.

As an alternative embodiment of the present invention, FIG. 12 illustrates a specially designed balloon catheter instead of the plurality of wire loops 36 to hold the stent 46 in place. As shown, prior to reaching the narrowed vascular region 76, an annular ring balloon 100 is inflated until an annular ring balloon diameter 106 sufficiently exceeds the vessel diameter 102 to suspend the forward movement of the stent-balloon catheter combination 86 through vessel 48. This embodiment could also be achieved using only one balloon catheter. This specially shaped catheter would be partially inflated before reaching the narrowed vascular region 76 so that the stent-balloon catheter combination 86 portion of the catheter was smaller in diameter than vessel diameter 102, including narrowed vascular region 76. But, the annular ring balloon 100 portion would, as before, have an annular ring balloon diameter 106 sufficiently exceeding the vessel diameter 102 to suspend the forward movement of the stent-balloon catheter combination 86 through vessel 48.

Figures 15A, 15B:
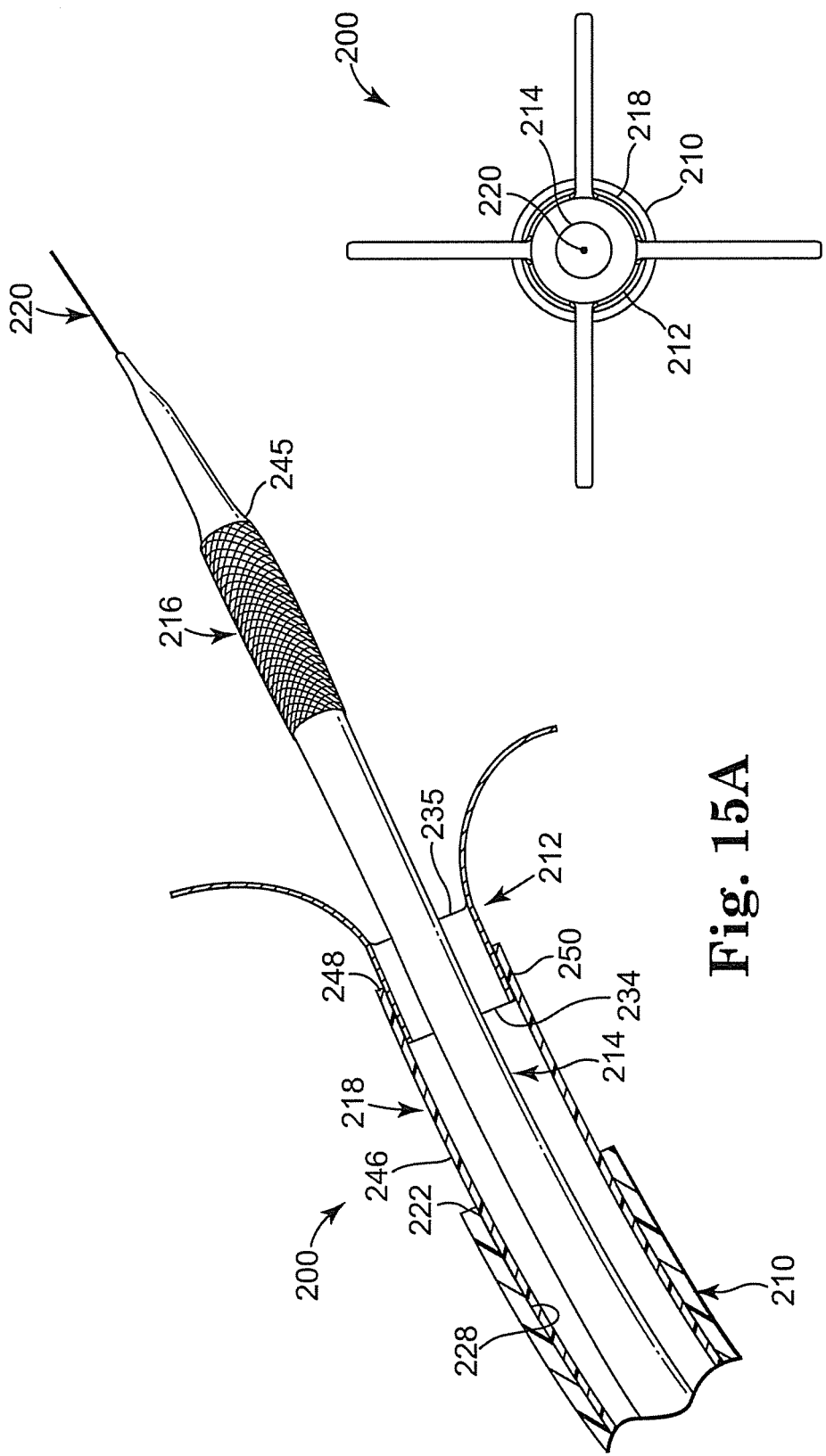
FIGS. 15A and 15B show an alternative embodiment stent placement system in accordance with the present invention.

Another embodiment of the present invention relates to a stent placement system 200 shown in FIGS. 15A and 15B. The system 200 is adapted for use with a guiding catheter 210 (shown in cross-section in FIG. 15A) and includes a deployment site locator 212 (shown in cross-section in FIG. 15A). In one embodiment, the deployment site locator 212 is used with a stent delivery device 214 configured to deliver a stent 216 (shown in perspective in FIG. 15A) that can be provided as part of the stent placement system 200, or as a separate component. In one embodiment, the stent placement system 200 further includes a carrier catheter 218 and guide wire 220 that is analogous to the balloon guide wire 62 (FIG. 7). The stent placement system 200, including its components and operation, is described in further detail below.

The guiding catheter 210 is analogous to the guiding catheter 40 (FIG. 5) previously described. The guiding catheter 210 forms a lumen 228, extending from a proximal end (not shown) to a distal end 222 of the guiding catheter 210. The lumen 228 is sized to facilitate delivery of the stent delivery device 214, the deployment site locator 212, and the carrier catheter 218 into the human body as described in greater detail below. It should be noted that the guiding catheter 210, or other catheters described herein, can be used in combination with a Toughy™ or other haemostatic valve.

Figure 16:
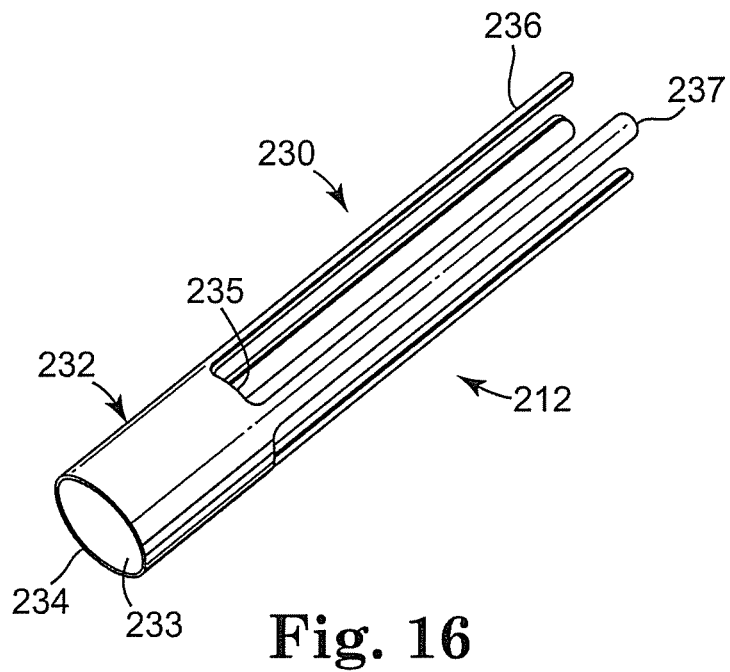
FIG. 16 illustrates a deployment site locator of the system of FIGS. 15A and 15B.

With additional reference to FIG. 16, the deployment site locator (or deployment site regulator) 212 preferably includes a plurality of rods 230 affixed to a base 232. As will be described in greater detail below, the deployment site locator 212 defines an expanded state (FIGS. 15A and 15B) wherein the plurality of rods 230 extend outward radially from the base 232. In one embodiment, the deployment site locator 212 naturally assumes the expanded state. Further, as shown in FIG. 16, the deployment site locator 212 can be transitioned to a collapsed state wherein the plurality of rods 230 extend substantially parallel to the base 232. By way of reference, the deployment site locator 212 preferably transitions to or defines the collapsed state as shown in FIG. 16 upon application of an external load or force such as by a guiding catheter (omitted in the view of FIG. 16).

In the one embodiment of FIG. 16, the base 232 forms a lumen 233 extending between a proximal end 234 and a distal end 235. The lumen 233 defines a central axis. The base 232 has an inner diameter and an outer diameter generally configured to allow insertion of the deployment site locator 212 within the guiding catheter 210 and to accept the stent delivery device 214.

As shown in FIG. 16, the base 232 is preferably contiguously formed with the plurality of rods 230. However, it is to be understood that alternative means of affixing the plurality of rods 230 to the distal end 235 of the base 232 may otherwise be employed, such as interference fits, gluing, or welding. Although FIG. 16 shows the deployment site locator 212 as including four of the rods 230, it is to be understood that various numbers of rods are contemplated, either greater or less than four, within the scope of the present invention.

In one embodiment, both the base 232 and plurality of rods 230 are formed of a nickel-titanium alloy or under more general nomenclature, NiTi or Nitinol™. The deployment site locator 212 can be formed from a Nitinol™ tube, laser cut as to form the plurality of rods 230 at an end of the tube. In a preferred embodiment, a distal portion 236 of each of the plurality of rods 230 is free standing or separated from the others, with each rod 230 terminating in a distal end 237. Further, the deployment site locator 212 preferably includes a radio-opaque material. In one embodiment, each of the plurality of rods 230 comprises of the radio-opaque material (not shown in FIG. 16). More specifically, it is preferential that at least a portion of each of the plurality of rods 230 be covered with the radio-opaque material.

Figure 17:
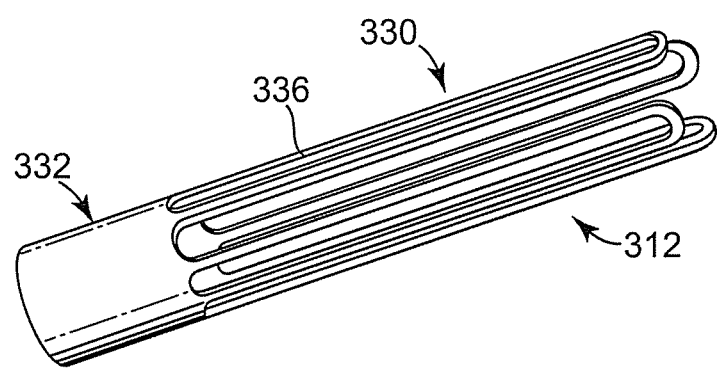
FIG. 17 illustrates an alternative embodiment deployment site locator in accordance with the present invention.

As shown in FIG. 16, the plurality of rods 230 are, in one embodiment, solid with a arcuate cross-section. However, an alternative embodiment deployment site locator 312 is shown in perspective in FIG. 17 and includes a plurality of rods 330 extending from a base 332. In the embodiment of FIG. 17, each of the plurality of rods 330 has a central aperture 336. In the alternative embodiment, the rods 330 are contiguously formed with the base 332; however, it is to be understood that the rods 330 may be affixed to the base 332 by a variety of means including those previously described or their equivalents.

Figure 18A:
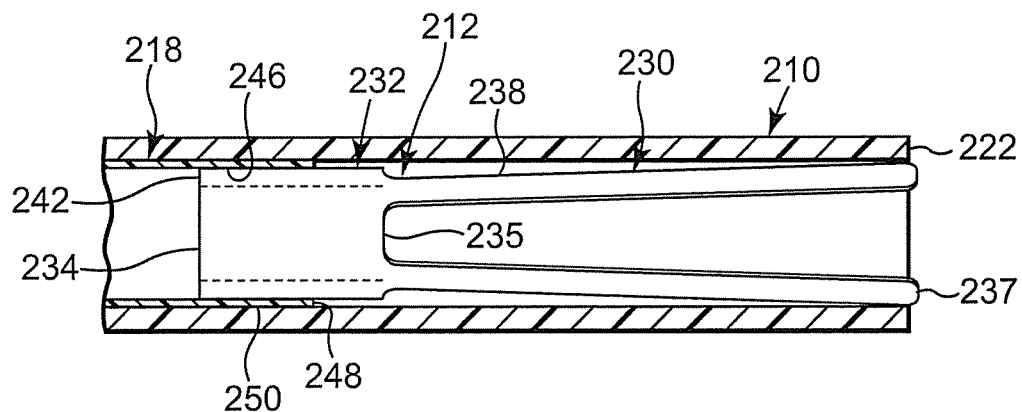
FIG. 18A is an enlarged, cross-sectional view of the system of FIG. 15A in a collapsed state.
Figure 18B:
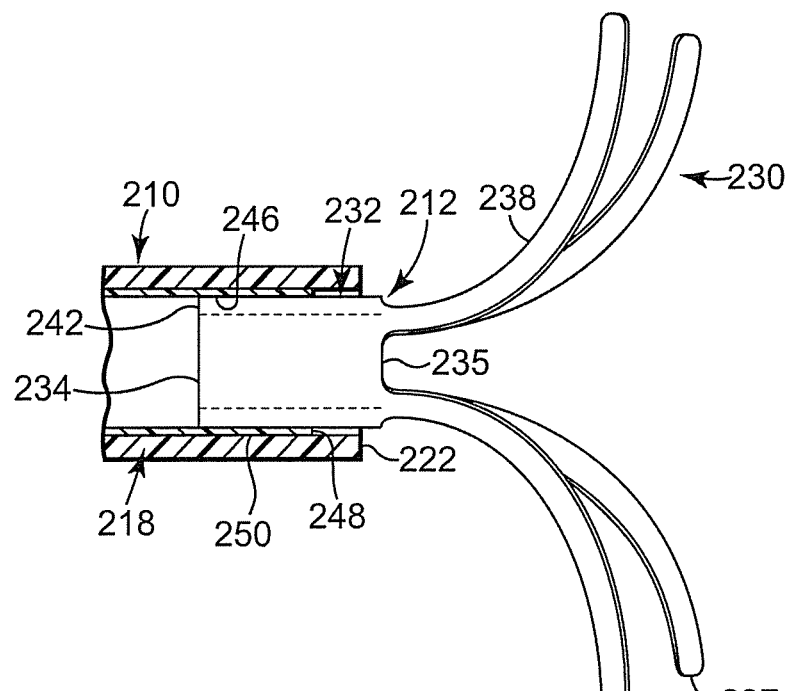
FIG. 18B is an enlarged, cross-sectional view of the system of FIG. 15A in an expanded state.

With reference to FIGS. 18A and 18B, the deployment site locator 212 (shown in perspective) is configured to be transitionable between a collapsed state (FIG. 18A) and an expanded state (FIG. 18B). In particular, it is preferable that the expanded state includes the plurality of rods 230 extending outward radially relative to one another and the collapsed state includes the plurality of rods 230 being less outwardly extended relative to one another than in the expanded state. The capability to transition between states is especially advantageous for insertion into the human body via the guiding catheter 210 (shown in cross-section) as the deployment site locator 212 presents a smaller profile during insertion in the collapsed state.

In one preferred transitionable configuration, a spring action is incorporated into each of the plurality of rods 230 such that each of the plurality of rods 230 extend outward radially from one another in an unloaded, or natural state, but may be loaded, or deflected inward to present a smaller profile. In one embodiment the spring action is physically incorporated into each of the plurality of rods 230. For example, in one embodiment, each of the plurality of rods 230 is formed to have a thin layer of material removed from an outer surface 238 thereof. Thus, each of the plurality of rods 230 has a thickness that is tapered relative to a thickness 242 of the base 232. It is to be noted that other methods of accomplishing the transitionable configuration are possible. For example, the deployment site locator 212 may be comprised of heat treated materials.

In FIG. 18A, each of the plurality of rods 230 is shown under an external load supplied by an inner diameter of the guiding catheter 210 (shown in cross-section). By comparing FIGS. 18A and 18B, it can be understood that the deployment site locator 212 can be transitioned to a collapsed state by retracting the plurality of rods 230 within the guiding catheter 210. In particular, the retraction of the plurality of rods 230 into the guiding catheter 210 applies an external load to the plurality of rods 230 which forces them toward one another. It is to be understood that, upon removal of the external load the plurality of rods 230 are configured to self-transition to the expanded state.

In FIG. 18B, the deployment site locator 212 is shown unloaded in the expanded state with the plurality of rods 230 extended from the guiding catheter 210. In the preferred embodiment, the expanded state is such that the distal end 237 of each of the plurality of rods 230 are separated farther from one another than in the loaded or collapsed state. Preferably, the deployment site locator 212 is configured such that the plurality of rods 230 extend outward radially substantially perpendicular to the central axis of the base 232 in the expanded state and, in the collapsed state, the plurality of rods 230 extend substantially parallel to the central axis of the base 232. By way of reference, FIGS. 18A and 18B illustrate one embodiment in which the distal ends 237 of the rods 230 are distal to the distal end 235 of the base 232 in both the collapsed state (FIG. 18A) and the expanded state (FIG. 18B). Alternatively, the deployment site locator 212 can be configured such that the distal ends 237 of the rods 230 are proximal the distal end 235 of the base 232 in one or both of the collapsed and expanded states. For example, the rods 230 can be oriented relative to the base 232 in a manner akin to that shown for the loops 35 in FIG. 10. Regardless, in the collapsed state, the rods 230 are oriented such that a minimal radial spacing exists between the distal end 237 of each of the rods 230 and the distal end 235 of the base 232, and in the expanded state, the distal ends 237 of the rods 230 are radially outwardly spaced relative to the distal end 235 of the base 232 due to the radially outward extension of the rods 230 from the base 232.

As shown in FIGS. 15A and 15B, the stent delivery device 214 is analogous to those associated with embodiments of the present invention previously described (for example, as shown in FIG. 5). The stent delivery device 214 preferably includes a balloon 245 capable of expanding the stent 216. The general operation of the stent delivery device 214, as a part of the stent placement system 200, is described in further detail below.

With additional reference to FIG. 18A, the carrier catheter 218 (shown in cross-section) can be described. In general, the carrier catheter 218 forms a lumen 246 and is configured to be coaxially located within the guiding catheter 210. In one preferred embodiment, the carrier catheter 218 has a smaller outer diameter than the inner diameter of the guiding catheter 210. The carrier catheter 218 extends a length from a proximal end (not shown) to a distal end 248. In one preferred embodiment, a distal portion 250 of the carrier catheter 218 is configured to form an interference fit with the proximal end 234 of the base 232 of the deployment site locator 212. The carrier catheter 218 is preferably longer than the guiding catheter 210 and shorter than the stent delivery device 214 in order to allow each, in turn, to be manipulated from outside the human body. With this arrangement, a surgeon or other operator can move a proximal end (not shown) of the carrier catheter 218 relative to a proximal end (not shown) of the guiding catheter 210 from outside of the body such that when the deployment site locator 212 is affixed to the distal end 248, the deployment site locator 212 can be at least partially extended from the distal end 222 of the guiding catheter 210.

The general interrelation of the preferred stent placement system 200 elements and the guiding catheter 210 is described below. Generally, the guide wire 220 is disposed within the stent delivery device 214; which is, in turn, disposed within the carrier catheter 218 and deployment site locator 212 (in the collapsed state); which are, in turn, disposed within the guiding catheter 210. A method of deploying the stent 216 using a preferred embodiment of the above-described system also follows, which should additionally illustrate the interrelation of the above-described components.

As shown in FIGS. 18A and 18B, the carrier catheter 218 is preferably slidably engaged within the guiding catheter 210 such that the carrier catheter 218 is coaxially disposed within the guiding catheter 210. As previously mentioned, the deployment site locator 212 is preferably affixed to the distal end 248 of the carrier catheter 218. In the preferred embodiment shown, the proximal end 234 of the base 232 of the deployment site locator 212 is located within the distal portion 250 of the carrier catheter 218 in an interference fit. However, it is to be noted that other means of affixing the deployment site locator 212 at the distal end 248 of the carrier catheter 218 can be employed, such as gluing, welding, or contiguous formation. Regardless, it is preferable that the deployment site locator 212 be slidably engaged within the guiding catheter 210 as well. In particular, the carrier catheter 218 and deployment site locator 212 are preferably coaxially disposed within the guiding catheter 210, such that the deployment site locator 212 may be slid, or extended distally, from the guiding catheter 210 to allow transition to the expanded state and then retracted into the guiding catheter 210 to transition back to the collapsed state.

As described in other embodiments of the present invention, it may be preferable to affix the deployment site locator 212 relative the stent delivery device 214, and in particular relative to the stent 216. Alternatively, in a preferred embodiment, at least a portion of the stent delivery device 214 is slidably engaged within a portion of the deployment site locator 212. In the preferred embodiment shown in FIGS. 15A and 15B, the stent delivery device 214 is coaxially disposed within the base 232 of the deployment site locator 212 as well as the carrier catheter 218. In particular, the stent delivery device 214 is preferably slidably engaged within the base 232, such that the stent delivery device 214 can be extended distally from the deployment site locator 212. In this manner, the deployment site locator 212 is adjustably located relative the stent 216 rather than fixed relative to the stent 216. It is to be further noted that in the preferred embodiment, the plurality of rods 230 do not interfere with such extension when the deployment site locator 212 is in the expanded state as shown.

FIGS. 19A-19E illustrate use of the system 200 to deploy the stent 216 within a vessel 252 adjacent an ostium 251 thereof. First, the guiding catheter 210, and in particular the distal end 222 thereof, is delivered to the vessel 252 along with the guide wire 220. One preferred method of delivering the distal end 222 of the guiding catheter 210 adjacent to the ostium 251, as well as disposing the guide wire 220 within the vessel 252, includes first placing the guiding catheter 210 in the vessel 48 (FIG. 4) to be used as an access point into a human body. A 0.35 J tip wire (not shown) is then placed inside the guiding catheter 210 and with the aid of the J tip wire and under fluoroscopic or x-ray guidance, positioning the guiding catheter 210 near the ostium 251 of the vessel 252 to be stented. The J tip wire is removed. Then the distal end 222 of the guiding catheter 210 is rotated or positioned so as to engage the ostium 251. The guide wire 220 is then threaded through the guiding catheter 210 forward into the vessel 252 to be stented. It will be recognized that other techniques for delivering the guiding catheter 210 and the guide wire 220 are equally acceptable.

Figure 19A:
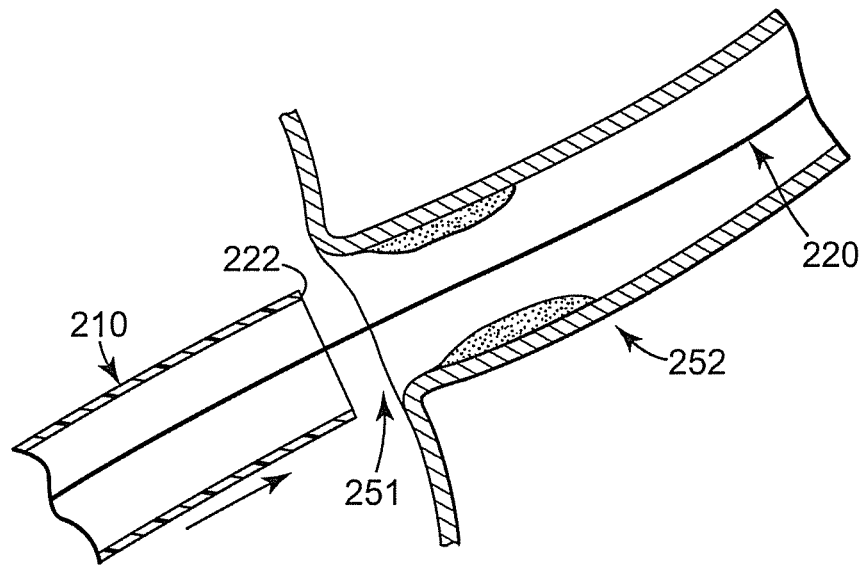
FIGS. 19A-19E illustrate a method of placing an intravascular stent using the stent placement system of FIG. 15A.

As is shown in FIG. 19A, the guiding catheter 210 is then withdrawn slightly from the ostium 251. The deployment site locator 212 (FIG. 18A) is then guided to the distal end 222 of the guiding catheter 210. One preferred method of guiding the deployment site locator 212 through the guiding catheter 210 includes threading the deployment site locator 212 over the guide wire 220 and through the guiding catheter 210 to the target site. It is to be noted that, in the preferred embodiment, the deployment site locator 212 is maintained in the collapsed state (FIG. 18A) while being guided through the guiding catheter 210 by the inner diameter of the guiding catheter 210.

Figure 19B:
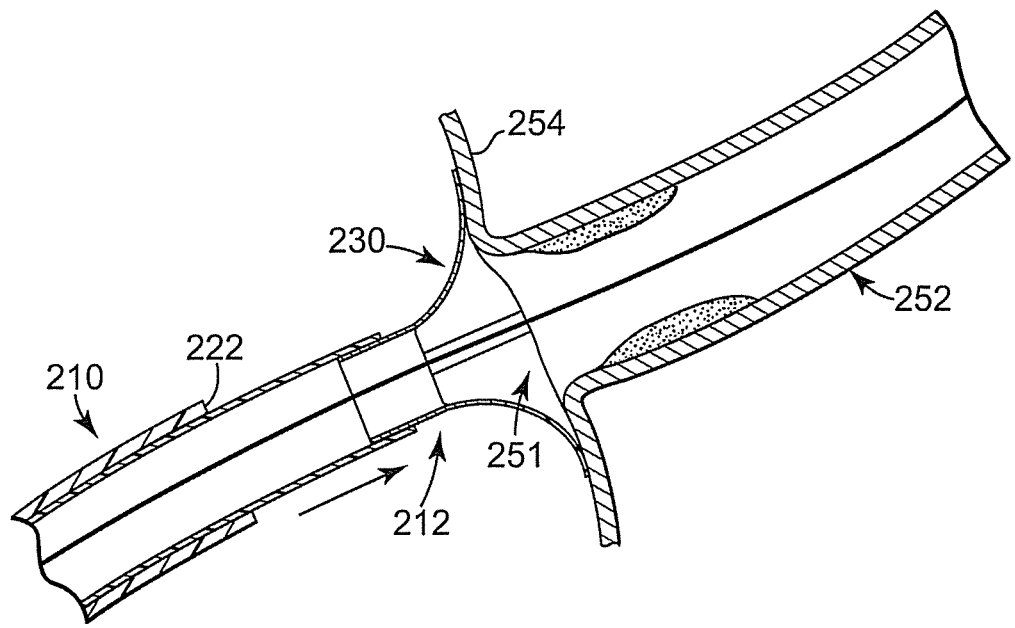

The deployment site locator 212 is then distally advanced slightly from the distal end 222 of the guiding catheter 210 such that deployment site locator 212 transitions to the natural or expanded state and the plurality of rods 230 extend outward radially from one another. This relationship is shown, for example, in FIG. 18B. Once again, the expanded state can include the distal ends 237 of the rod 230 being distal the distal end 235 of the base 232 as shown in FIG. 18B, or the distal ends 237 of the rods can be proximal, or even aligned with, the distal end 235 of the base 232. Regardless, once the deployment site locator 212 has been distally extended and expanded, the deployment site locator 212 and/or guiding catheter 210 is maneuvered toward the ostium 251 until at least one of the plurality of rods 230 contact the vascular structures 254 adjacent the ostium 251. As a point of reference, the surface area interaction or interface between individual ones of the rods 230 and the vascular structures 254 can be more or less than that illustrated in FIG. 19B. FIG. 19B illustrates the deployment site locator 212 after having been guided through the guiding catheter 210 to contact the ostium 251. The surgeon may observe the contact by feel, x-ray, or other physical or visual indicator. Once the contact has been observed, the surgeon has effectively determined a position of the ostium 251.

Figure 19C:
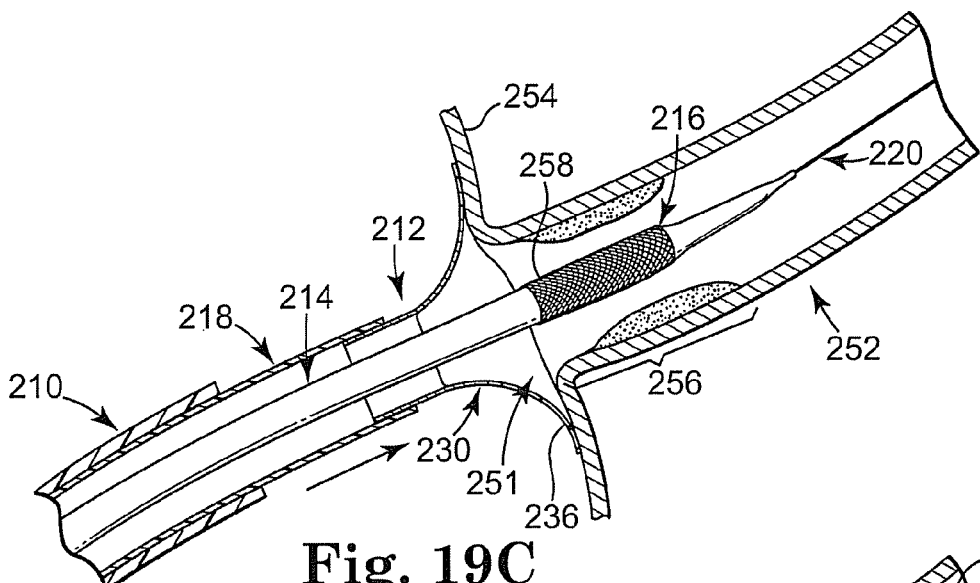

In a preferred embodiment, the stent delivery device 214 is slidably engaged within the deployment site locator 212 and carrier catheter 218. With the deployment site locator 212 now in contact with the vascular structure 254, the stent delivery device 214, and the stent 216 removably affixed thereto, are advanced over the guide wire 220, thorough the guiding catheter 210 and the carrier catheter 218. The stent 216 is directed through the deployment site locator 212 and then distally into the vessel 252 to be stented. As is shown in FIG. 19C, subsequent to extending the stent delivery device 214 into the vessel 252, the stent delivery device 214 is partially disposed within the deployment site locator 212 with the stent 216 located proximate the determined position of the ostium 251.

Once the stent 216 is proximate the ostium 251, the stent 216 is delivered to a desired stent location 256. The desired stent location 256 is preferably defined such that a proximal end 258 of the stent 216 is located at the ostium 251 of the vessel 252 to be stented. However, it is to be understood that the present invention is also capable of allowing a surgeon to select alternative desired stent locations relative the ostium 251.

A preferred method of delivering the stent 216 to the desired stent location 256 relative to the ostium 251 includes visual determination of a position of both the deployment site locator 212 and the stent 216. In particular, x-ray imaging or other imaging techniques are used to determine the position of the deployment site locator 212 and the position of the stent 216. Thus, in accordance with one preferred methodology, at least one of the plurality of rods 230 is contacted with the vascular structures 254. The positions of the deployment site locator 212 and stent 216 are then determined by visual indication. Finally, the position of the stent 216 is adjusted relative to the deployment site locator 212 such that the stent 216 is delivered to the desired stent location 256 chosen.

In a preferred embodiment, adjusting the position of the stent 216 relative to the deployment site locator 212 includes visually confirming that at least one radio-opaque marker (not shown) associated with the stent 216 is aligned with at least one radio-opaque marker (not shown) associated with the deployment site locator 212 and in particular the rod(s) 230. This method is particular advantageous for precisely locating a stent at the desired stent location 256. As previously described, the radio-opaque marker associated with the deployment site locator 212 is preferably defined by radio-opaque material covering the distal portion 236 of each of the plurality of rods 230. In this manner, a radio-opaque marker at a proximal end 258 of the stent 216 can be aligned with the distal portion 236 of each of the plurality of rods 230 in contact with the vascular structures 254. One particular advantage of this method is that the proximal end 258 of the stent 216 can be located precisely at the ostium 251 of the vessel 252 to be stented at the preferred desired stent location 256.

Figure 19D:
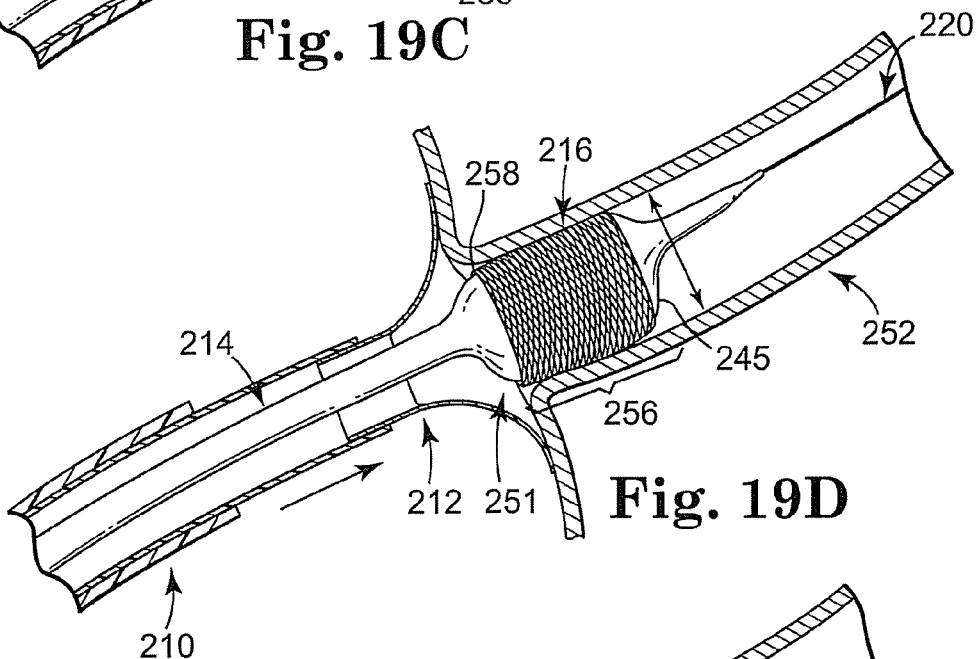

Once the stent 216 is positioned, the balloon 245 is then expanded and the stent 216 is thereby expanded and deployed. FIG. 19D illustrates the stent 216 delivered and deployed at the desired stent location 256. Following deployment, the balloon 245 is deflated to allow removal of the stent delivery device 214. In a preferred method, the balloon 245 is deflated and is pulled back through the deployment site locator 212 and removed from the body while leaving the guide wire 220 in place.

It should be noted that in an alternative embodiment of the instant preferred method, the stent 216 is fixed relative to the deployment site locator 212. In this configuration, the position of the ostium 251 is determined by contacting the deployment site locator 212 with the vascular structures 254 surrounding the ostium 251. In this manner, the desired stent location 256 is still based upon the determination of the position of the ostium 251. However, the stent 216 is delivered within the vessel 252 at a fixed distance from the deployment site locator 212.

Figure 19E:
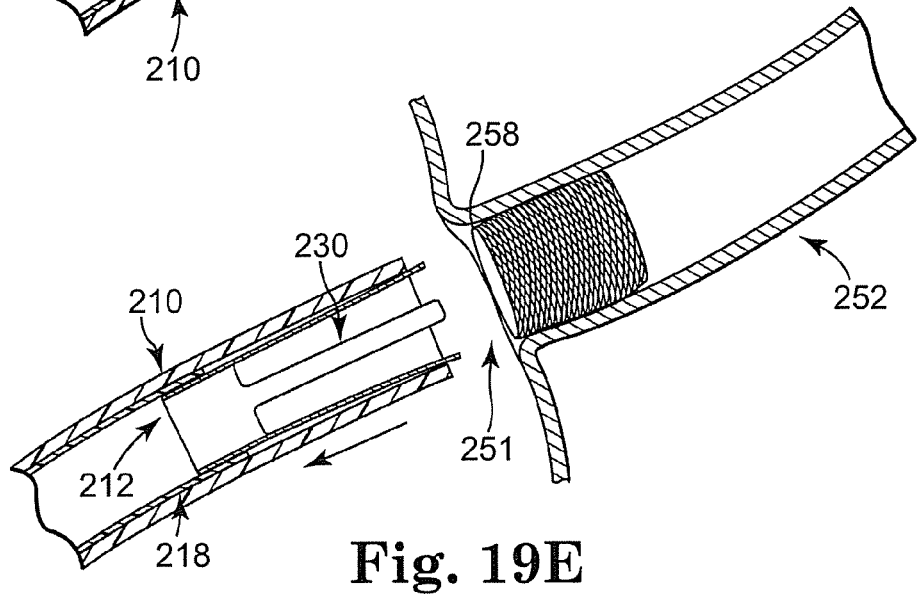

A preferred method of retracting the deployment site locator 212 from the ostium 251 and out of the body includes manipulating the proximal end (not shown) of the carrier catheter 218 such that the deployment site locator 212 is pulled back, or retracted, into the guiding catheter 210 and then removed from the patient. In FIG. 19E, the plurality of rods 230 of the deployment site locator 212 are shown partially transitioned back to the collapsed state following partial retraction into the guiding catheter 210. Once again, it can be seen that the capability of the deployment site locator 212 to transition between the expanded and the collapsed state is particularly advantageous for removal from the body.

Thus, the present invention provides improved stent placement within the deployment site of a narrowed blood vessel during a stent procedure. Notably, the deployment site locator 212 is preferably configured to maintain its structural integrity over repeated transitions between the collapsed and expanded states, and thus is highly amenable for re-use.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof. For example, while the deployment site locator 212 has been preferably described as being a component separate from, and moveable relative to, the guiding catheter 210, other configurations are also acceptable. For example, the deployment site locator can be formed as a distal portion of the guiding catheter, either as an integral segment of the guiding catheter or as a separate body attached to the distal end of the guiding catheter. Regardless, an outer hub can further be provided that is slidably received over the deployment site locator for effectuating transition between the collapsed and expanded states.

What is claimed is:

1. A stent placement system for use with a guiding catheter as part of a stent procedure, the stent placement system comprising:
   a deployment site locator coaxially received within the guiding catheter, the deployment site locator including:
      a base, and
      a plurality of rods affixed to the base, each one of the plurality of rods being a solid body and having a distal end, wherein the deployment site locator is adapted to provide an expanded state in which the plurality of rods extend radially outward from the base to contact vascular structures, wherein each one of the plurality of rods is configured to self-transition from a collapsed state toward the expanded state;
   a carrier body coaxially received within the guiding catheter such that the carrier body and the deployment site locator are longitudinally slidable relative to the guiding catheter, wherein the base is affixed to a distal end of the carrier body;
   a stent delivery device coaxially received within the carrier body; and
   a stent carried by the stent delivery device such that the stent delivery device and the stent are longitudinally slidable relative to the carrier body and the deployment site locator, wherein the deployment site locator is a component separate from the stent, and further wherein the deployment site locator is movable relative to the stent.

2. The stent placement system of claim 1, wherein the carrier body is a catheter.

3. The stent placement system of claim 2, wherein the deployment site locator is affixed to the distal end of the carrier catheter via an interference fit.

4. The stent placement system of claim 1, wherein the deployment site locator is configured such that a relative position of the stent and the deployment site locator is determinable via a visual indication.

5. The stent placement system of claim 4, wherein the visual indication includes x-ray imaging.

6. The stent placement system of claim 4, wherein the deployment site locator includes radio-opaque material.

7. The stent placement system of claim 6, wherein the plurality of rods include radio-opaque material.

8. The stent placement system of claim 7, wherein a portion of each of the plurality of rods is covered by radio-opaque material.

9. The stent placement system of claim 1, wherein the deployment site locator is capable of transitioning between the expanded state and a collapsed state, and further wherein outward radial extension of the rods relative to one another in the collapsed state is less than outward radial extension of the rods relative to one another in the expanded state.

10. The stent placement system of claim 9, wherein the distal ends of the plurality of rods are free standing, and further wherein the distal ends are spaced farther apart from one another in the expanded state than in the collapsed state.

11. The stent placement system of claim 9, wherein the deployment site locator is configured to transition between the collapsed state and the expanded state via spring action.

12. The stent placement system of claim 9, wherein each of the plurality of rods has an outer thickness that is tapered relative to the base.

13. The stent placement system of claim 9, wherein the distal ends of the rods are distal a distal end of the base in the collapsed state.

14. The stent placement system of claim 9, wherein the carrier body extends a length greater than a length of the guiding catheter, such that a proximal end of the carrier body is capable of being moved relative a proximal end of the guiding catheter to transition the deployment site locator between the expanded stated and the collapsed state.

15. The stent placement system of claim 1, wherein the deployment site locator is configured such that the plurality of rods self-transition from the collapsed state to the expanded state upon removal of an external load.

16. The stent placement system of claim 1, wherein each of the plurality of rods has an arcuate cross-section.

17. The stent placement system of claim 1, wherein the base has a ring shape.

18. The stent placement system of claim 1, wherein the stent placement system further comprises:
   a guidewire slidably receivable within the stent delivery device.

19. The stent placement system of claim 1, wherein the stent placement system is configured such that in response to a longitudinal force applied to the carrier body sufficient to longitudinally move the carrier body relative to the guiding catheter, the base is caused to move in tandem with the carrier body relative to the guiding catheter.

* * * * *